United States Patent
AbuSalim et al.

(10) Patent No.: US 11,597,889 B2
(45) Date of Patent: *Mar. 7, 2023

(54) PRODUCTION OF HIGH-VALUE FUEL MIXTURES FROM SYNTHETIC AND BIOLOGICALLY DERIVED HYDROCARBON MOLECULES

(71) Applicant: ExxonMobil Technology and Engineering Company, Annandale, NJ (US)

(72) Inventors: Deyaa I. AbuSalim, Morristown, NJ (US); Eugine Choi, Flemington, NJ (US); Kun Wang, Branchburg, NJ (US); Himanshu Gupta, Clinton, NJ (US); Dongil Kang, Westfield, NJ (US); Jung Park, Maplewood, NJ (US); Jonathan E. Mitchell, Easton, PA (US)

(73) Assignee: EXXONMOBIL TECHNOLOGY AND ENGINEERING COMPANY, Annandale, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/119,096

(22) Filed: Dec. 11, 2020

(65) Prior Publication Data

US 2021/0189276 A1 Jun. 24, 2021

Related U.S. Application Data

(60) Provisional application No. 62/952,612, filed on Dec. 23, 2019.

(51) Int. Cl.
| | | |
|---|---|---|
| *C10L 10/10* | (2006.01) | |
| *C07C 407/00* | (2006.01) | |
| *C10L 1/04* | (2006.01) | |
| *C07C 2/86* | (2006.01) | |
| *C07C 29/48* | (2006.01) | |
| *C10G 29/20* | (2006.01) | |
| *C10G 50/00* | (2006.01) | |

(52) U.S. Cl.
CPC ............. *C10L 10/10* (2013.01); *C07C 2/862* (2013.01); *C07C 29/48* (2013.01); *C07C 407/00* (2013.01); *C10G 29/205* (2013.01); *C10G 50/00* (2013.01); *C10L 1/04* (2013.01); *C10G 2300/305* (2013.01); *C10G 2400/02* (2013.01); *C10L 2200/0423* (2013.01); *C10L 2200/0453* (2013.01)

(58) Field of Classification Search
CPC .... C10L 10/10; C10L 1/04; C10L 2200/0423; C10L 2200/0453; C10L 2270/023; C07C 2/862; C07C 29/48; C07C 407/00; C10G 29/205; C10G 50/00; C10G 2300/305; C10G 2400/02
See application file for complete search history.

(56) References Cited

U.S. PATENT DOCUMENTS

| | | | | |
|---|---|---|---|---|
| 8,476,479 | B2* | 7/2013 | Fujiyama | C10G 3/57 |
| | | | | 585/242 |
| 9,637,423 | B1* | 5/2017 | Wang | C07C 29/132 |
| 9,637,424 | B1* | 5/2017 | Wang | C10L 10/10 |
| 9,688,626 | B2* | 6/2017 | Wang | C07C 2/84 |
| 10,023,533 | B2* | 7/2018 | Wang | C07C 2/862 |
| 10,894,927 | B2* | 1/2021 | Karvo | C10L 1/026 |
| 2008/0015395 | A1* | 1/2008 | D'amore | C07C 41/06 |
| | | | | 568/697 |
| 2011/0319683 | A1* | 12/2011 | Abhari | C07C 9/14 |
| | | | | 585/16 |
| 2013/0338414 | A1* | 12/2013 | Fingland | C10G 45/62 |
| | | | | 585/310 |
| 2016/0168048 | A1* | 6/2016 | Wang | C10G 69/126 |
| | | | | 585/310 |
| 2017/0101355 | A1* | 4/2017 | Wang | C10G 50/02 |
| 2017/0101356 | A1* | 4/2017 | Wang | C07C 29/50 |
| 2017/0101357 | A1* | 4/2017 | Wang | C07C 407/00 |
| 2017/0101366 | A1* | 4/2017 | Wang | C10G 69/126 |
| 2019/0093035 | A1* | 3/2019 | Malatak | C10L 1/04 |

FOREIGN PATENT DOCUMENTS

| | | | |
|---|---|---|---|
| JP | 2017125113 A | * 7/2017 | |
| WO | WO-2009152495 A2 | * 12/2009 | ................ C10L 1/04 |

* cited by examiner

*Primary Examiner* — Pamela H Weiss
(74) *Attorney, Agent, or Firm* — Shook, Hardy & Bacon L.L.P.

(57) ABSTRACT

A process for converting light paraffins and/or light hydrocarbons to a high octane gasoline composition is disclosed. The process involves: (1) oxidation of iso-paraffins to alkyl hydroperoxides and alcohol; (2) conversion of the alkyl hydroperoxides and alcohol to dialkyl peroxides; and (3) radical coupling of one or more iso-paraffins and/or iso-hydrocarbons using the dialkyl peroxides as radical initiators, thereby forming a gasoline composition comprising gasoline-range molecules including a C7 enriched gasoline composition having a road octane number (RON) greater than 100.

16 Claims, No Drawings

US 11,597,889 B2

PRODUCTION OF HIGH-VALUE FUEL MIXTURES FROM SYNTHETIC AND BIOLOGICALLY DERIVED HYDROCARBON MOLECULES

CROSS-REFERENCE TO RELATED APPLICATIONS

This application claims the benefit of U.S. Provisional Application No. 62/952,612, filed on Dec. 23, 2019, the entire contents of which are incorporated herein by reference.

FIELD OF THE INVENTION

The disclosure provides a process for converting light paraffins and/or light hydrocarbons to a high octane gasoline composition. The process involves: (1) oxidation of iso-paraffins to alkyl hydroperoxides and alcohol; (2) conversion of the alkyl hydroperoxides and alcohol to dialkyl peroxides; and (3) radical coupling of one or more iso-paraffins and/or iso-hydrocarbons using the dialkyl peroxides as radical initiators, thereby forming a gasoline composition comprising gasoline-range molecules including a C7 enriched gasoline composition having a road octane number (RON) greater than 100.

BACKGROUND OF THE INVENTION

The present disclosure relates to a process to upgrade light paraffins or hydrocarbons, e.g., $C_2$-$C_5$, to high-octane gasoline. The process is particularly applicable to the upgrading of iso-paraffins and iso-alkanes, which are abundantly found in Natural Gas Liquids (NGL) and tight oils (produced from shale or sandstone), as well as fractions from various refining and/or chemical streams or which are obtained through bio-fuel sources, such as vegetable oil.

With the increasing production of shale gas and tight oils, the supply of light paraffins (e.g., $C_2$-$C_8$, especially $C_2$-$C_5$ paraffins) is increasing at an unprecedented rate in the North America region; a large fraction (up to 30%) of NGL (Natural Gas Liquids), for example, is $C_4$/$C_5$ paraffins. At the same time, demand for $C_4$/$C_5$ molecules is decreasing due to a number of factors: (1) steam crackers switching feed from light naphtha to ethane; (2) shrinkage of the gasoline pool in the North American market; and (3) a potential mandate for gasoline Reid Vapor Pressure (RVP) reduction. Although diluent use of $C_5$s for heavy crude is predicted to grow somewhat, the supply of $C_4$s/$C_5$s is quickly outpacing demand and the imbalance will become worse with time.

Profitable dispositions for ethane (e.g., cracking to make ethylene) and propane (e.g., dehydrogenation to make propylene) exist. Upgrading $C_4$/$C_5$ paraffins to higher value and large volume products, while desirable, remains challenging. Conversion of $C_4$/$C_5$ paraffins to heavier hydrocarbon products such as gasoline, kerojet, diesel fuels, and lubricant basestocks would provide a large volume and higher value outlet to help alleviate the excess of light ends in the North American market. But there is no current commercial process directly converting light paraffins to heavier hydrocarbons such as these. Conventional upgrading practices first convert light paraffins to olefins via cracking or dehydrogenation, followed by olefin chemistries such as oligomerization or polymerization, alkylation, etc., to build higher molecular weight molecules. A number of technologies are known to convert light paraffins to aromatics such as BTX (benzene, toluene, and xylenes), including the Cyclar™ process developed by UOP and the M2-Forming process developed by Mobil Oil Corporation.

Currently, modern automobile gasoline engines require high octane fuel, and the demand for high octane gasoline is expected to continue to grow. Current high octane molecules from refining processes include aromatics, oxygenates, and alkylates. Current gasoline molecules from refining processes, with the exception of toluene, have a road octane number less than 110, such as the following typical road octane values: iso-butane 99.8; 2,3-dimethylbutane 100; 2,2,3-trimethylbutane 107.1; C8 trimethyls 101.9; benzene 100.8; toluene 110.7; C8+ aromatics 108.5-96; MTBE 106.2; TAME 106.5; and ethanol 100.4. Although aromatic molecules typically offer high octane, particulate emissions are a concern. Oxygenated high octane gasoline molecules such as ethanol have lower energy content (e.g., ethanol has ~82% of the volumetric energy content of gasoline) and can cause compatibility problems at high blending ratios. There is no commercial process to produce non-aromatic, non-oxygenated molecules with higher than 102 road octane. As such, there still remains a need for a process for producing higher octane, non-aromatic, non-oxygenated gasoline molecules, especially a process using readily available feedstocks, such as light paraffins.

In recent years, processes have been developed for converting low-value paraffinic materials to high octane gasoline, high cetane gasoline and high-octane diesel light. U.S. Pat. Nos. 9,637,423 and 9,637,424 These processes involves: (1) oxidation of an iso-paraffin to alkyl hydroperoxide and alcohol; (2) converting the alkyl hydroperoxide and alcohol to dialkyl peroxide; (3) and radical coupling of iso-paraffins using the dialkyl peroxides as radical initiators, thereby forming gasoline-range molecules. These methods have been successful in achieving substantially $C_8$ gasolines using iso-butane starting materials. A need remains however for methods of forming high octane gasolines of different carbon numbers including $C_6$, $C_7$, $C_9$, and $C_{10}$ gasolines. Furthermore, a need remains for processes to produce high-octane bio-fuels from bio-component starting materials.

SUMMARY OF THE INVENTION

In at least one aspect, the disclosure provides a novel process for producing high octane gasoline from abundant light paraffins and light hydrocarbons. In one embodiment of the disclosure, the process involves: (1) oxidation of iso-paraffins to alkyl hydroperoxides and alcohol; (2) conversion of the alkyl hydroperoxides and alcohol to dialkyl peroxides; and (3) radical-initiated coupling of two or more light paraffins and/or light hydrocarbons using the dialkyl peroxides as radical initiators, thereby forming products comprising gasoline range molecules. Optional fractionation of the product can then isolate a gasoline fraction which is substantially a C7 fraction having a road octane (RON) greater than 100.

In another embodiment of the disclosure, the process involves (1) oxidizing iso-butane to t-butyl hydroperoxide and t-butyl alcohol; (2) converting the t-butyl hydroperoxide and t-butyl alcohol to di-t-butyl peroxide; and (3) radical-initiated coupling two or more light paraffins and/or light hydrocarbons using the di-t-butyl peroxide as a radical initiator to form products comprising gasoline range molecules.

In yet another embodiment of the present disclosure, a gasoline composition is disclosed comprising primarily $C_7$ gasoline components, e.g., 2,2,3,-trimethylbutane, and having a road octane number greater than 102 without the inclusion of aromatics or oxygenates.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

All numerical values within the detailed description and the claims herein are modified by "about" or "approximately" the indicated value, and take into account experimental error and variations that would be expected by a person having ordinary skill in the art.

The following terms are used to describe the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

As used herein the terms "light" as in "light paraffin" and "light hydrocarbon" refers to components having a lower molecular weight. In particular embodiments, the components have lower alkyl chain backbones. In specific embodiments, the components have between 2 and 10 carbon atoms. As used herein, the number of carbon atoms, or "carbon number," is commonly referenced using the notation C# wherein # is the number of carbon atoms.

As used herein, the term "enriched" as in "C7 enriched gasoline composition" refers to a composition comprising a majority of the enriched component. In particular embodiments, the enriched component is present in more than 50% of the composition; in more than 75% of the composition; in more than 80% of the composition; in more than 90% of the composition; in more than 95% of the composition; or in more than 99% of the composition. In the case of C7 enriched, high octane gasoline, the gasoline product comprises more C7 gasoline components than components of other carbon numbers.

As used herein the term "substantially free" as in "substantially free of sulfur" or "substantially free of fluoride" refers to the elution of analytes such that the analytes are eluted in the compositions, e.g., gasoline compositions, containing a quantity of the recited component of less than 20% by weight of the particular component as compared to the total composition. In certain embodiments, "substantially free" refers to less than 10%, less than 5%, less than 2% less than 1%, less than 0.5% or less than 0.1% by weight of the particular component as compared to the total composition. In certain other embodiments, "substantially free" refers to less than 1.0%, less than 0.7%, less than 0.5%, less than 0.4% less than 0.3%, less than 0.2% or less than 0.1% by weight of the particular component as compared to the total composition. In still other embodiments, "substantially free" refers to less than 1.0%, less than 0.7%, less than 0.5%, less than 0.4% less than 0.3%, less than 0.2% or less than 0.1% by weight of the particular component as compared to the total composition.

Process for Making High Octane Gasoline

The disclosure relates to a process for making high octane gasoline from light paraffins and/or light hydrocarbons. The process of the present disclosure involves three primary steps: (1) oxidizing one or more iso-paraffins to alkyl hydroperoxides and alcohol using air or oxygen; (2) converting the alkyl hydroperoxides and alcohol to dialkyl peroxide; and (3) radical-initiated coupling two or more light paraffins and/or light hydrocarbons using the dialkyl peroxide as a radical initiator to form products comprising gasoline range molecules. This products are then fractionated to isolate the gasoline fraction having a road octane number (RON) greater than 100.

In certain embodiments of the present disclosure, the iso-paraffin used for the formation of the radial initiator is iso-butane. The process proceeds as described generally above: (1) oxidizing the iso-butane to t-butyl hydroperoxide and t-butyl alcohol using air or oxygen; (2) converting the t-butyl hydroperoxide and t-butyl alcohol to di-t-butyl peroxide; and (3) radical-initiated coupling of two or more light paraffins and/or light hydrocarbons using the di-t-butyl peroxide as a radical initiator to form products comprising gasoline range molecules.

In particular embodiments of the present disclosure, the light parrafins coupled during the conversion step are a mixture are $C_3$-$C_8$ paraffins. In certain embodiments, the paraffins coupled during the conversion step are a mixture of $C_3$-$C_5$ paraffins. In particular embodiments, the paraffins coupled during the conversion step are a mixture of propane and isobutane paraffins; a mixture of isobutane and isopentane paraffins, or a mixture of propane and isopentane paraffins.

In particular embodiments of the present disclosure, the light hydrocarbons coupled during the conversion step are a mixture are $C_3$-$C_8$ hydrocarbons. In certain embodiments, the hydrocarbons coupled during the conversion step are a mixture of $C_3$-$C_5$ hydrocarbons. In particular embodiments, the hydrocarbons coupled during the conversion step are a mixture of propane and isobutane; a mixture of isobutane and isopentane, a mixture of propane and isopentane, or a mixture of propane, isobutane, and isopentane.

In certain embodiments, the composition of the product gasoline can be adjusted by varying the ratio of the hydrocarbons used in step 3. In particular embodiments when two hydrocarbons are used, the ratio of the first hydrocarbon to the second hydrocarbon is from a 99:1 to about 1:99; from about 75:1 to about 1:75; from about 50:1 to about 1:50; from about 5:1 to about 1:5; from about 2:1 to about 1:2; or about 1:1. In particular embodiments where three or more hydrocarbons are used, each hydrocarbon can be used in equal mol fractions.

In a particular embodiment, the disclosure provides a process for making a C7 enriched, high octane gasoline comprising the steps of: (1) oxidizing iso-butane to t-butyl hydroperoxide and t-butyl alcohol using air or oxygen; (2) converting the t-butyl hydroperoxide and t-butyl alcohol to di-t-butyl peroxide; and (3) radical-initiated coupling of propane paraffin and isobutane paraffin using the di-t-butyl peroxide as a radical initiator to form a gasoline product having a high concentration of 2,2,3-trimethyl-butane.

The chemistry of Steps 1-3 with respect to iso-butane feed is shown below in corresponding Equations 1-7. Equation 3 shows the mechanism of action in using the di-t-butyl peroxide as a radical initiator. Equations 4-7 show the radical-initiated coupling of various light hydrocarbons.

Equation 1

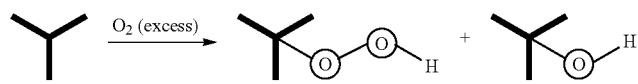

Equation 2

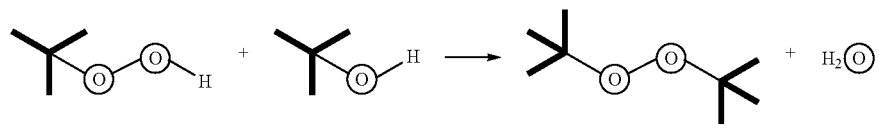

-continued
Equation 3
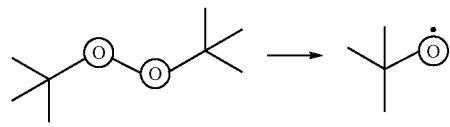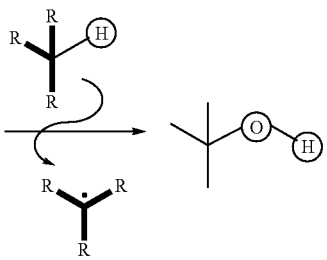
Equation 4-Propane and isobutane
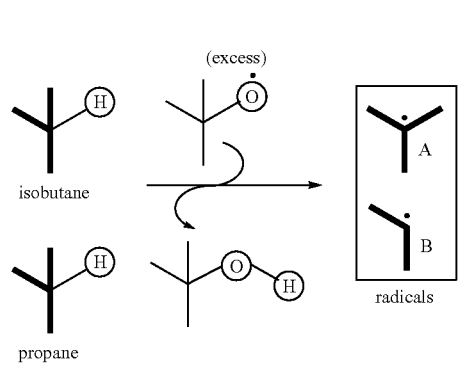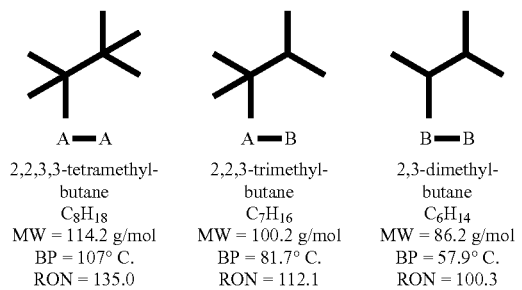
Equation 5-Isopentane and isobutane
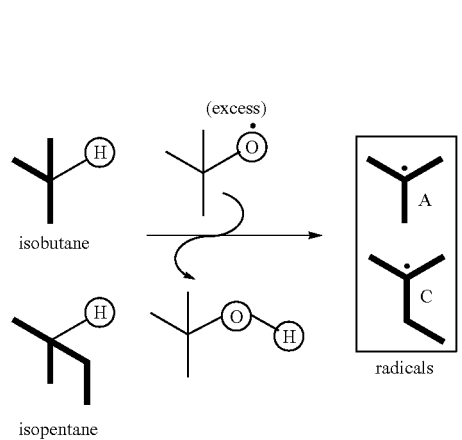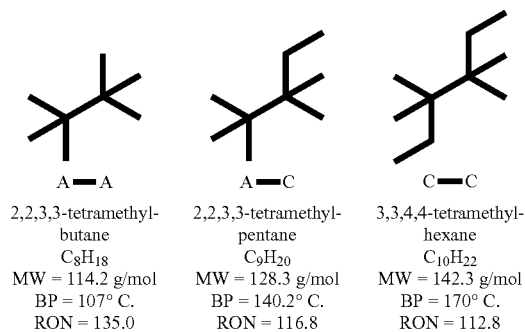
Equation 6-Propane and isopentane
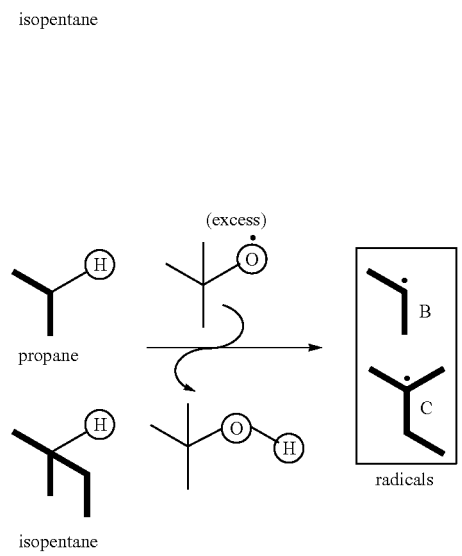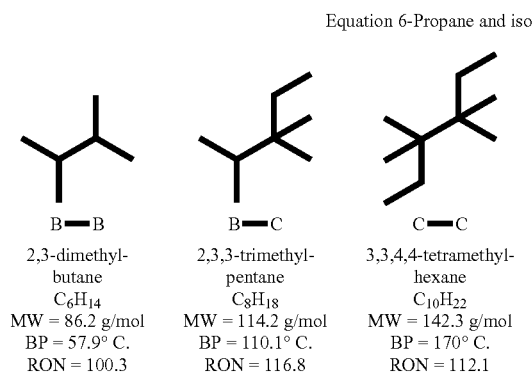

-continued

Equation 7-Propane, isobutane and isopentane

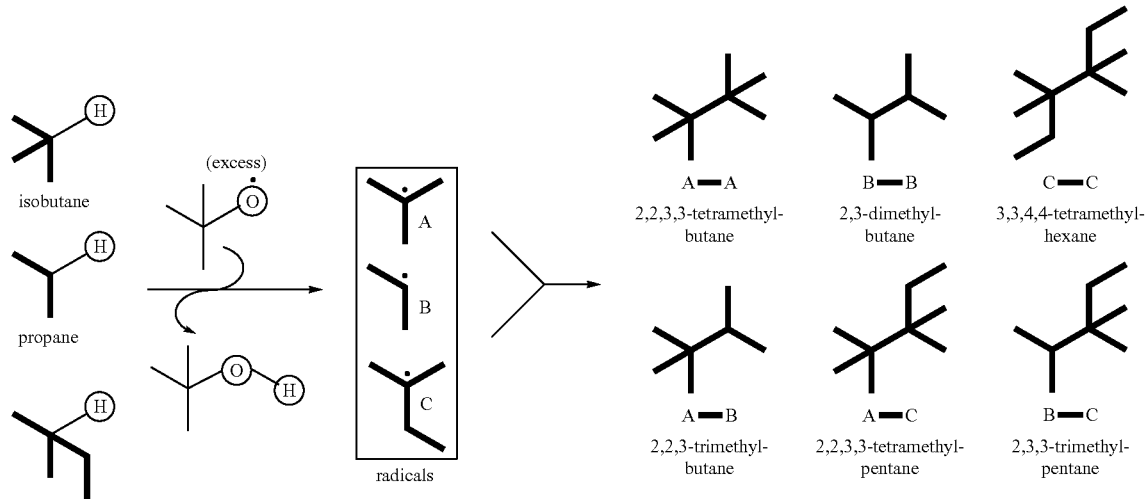

In another aspect, the disclosure provides a method of forming bio-fuels using the method of the disclosure. In particular embodiments, the methods of the disclosure utilize bio-components derived from vegetable oil in the feedstock. In such embodiments, vegetable oil is converted to straight chain hydrocarbons using hydrotreatment. The straight chain hydrocarbons are then isomerized and cracked into useful bio-molecules which can be used as feeds in the oxidative coupling products.

The use of biofuels is described in the following general scheme (Equation 8)

Equation 8

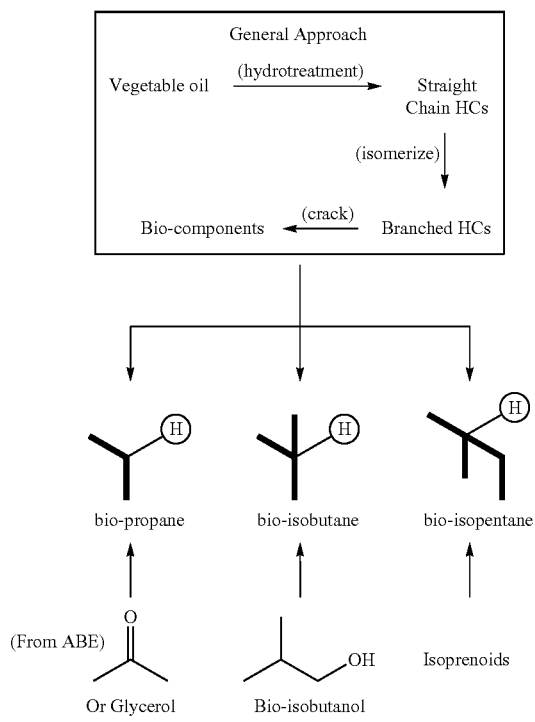

-continued

Targeted Approach

The methods of the disclosure can take advantage of two or more bio-feed chemicals, which can be obtained from one general, previously described, process. To accomplish this, vegetable oil can be converted to straight chain hydrocarbons via hydrotreament. The resulting hydrocarbons can then be isomerized and cracked into useful bio-molecules that can be used as feeds in the oxidative coupling process to make ultra-high octane, sulfur-free, bio-fuels. Additionally, specific components can be generated for use in this process. For example, the hydrotreatment of acetone (from ABE) or glycerol can yield bio-propane. Similarly, bio-isobutanol and isoprenoids can be processed to give the corresponding bio-isobutane and bio-isopentane, respectively. These bio-components can be used individually or as mixtures under our proposed oxidative coupling process to produce high-value, ultra-high octane bio-fuels.

The net reaction of the methods of the disclosure is oxygen (air) and hydrocarbons comprising high octane gasoline, as well as water and t-butyl alcohol.

The methods of the disclosure have the advantage of being substantially catalyst free. In particular embodiments the methods of the disclosure are catalyst free, i.e. performed without catalyst.

The methods of the disclosure have the advantage of producing a gasoline product which is substantially sulfur free and/or substantially fluoride free.

When propane and isobutane are used as starting materials in the feed, Step 3 is highly selective to 2,2,3-trimethylbutane, thus creating an overall C7 fraction having exceptionally high octane. By controlling the reaction severity for radical coupling (Equation 3), higher molecular weight materials can also be obtained. Depending on the nature of the iso-paraffin or iso-hydrocarbon used, the resulting alcohol can be used as high octane blend stock for gasoline. Alternatively, the alcohols can be converted via dehydration to olefins as chemical products (e.g., iso-butylene), oligomerized or alkylated to gasoline and/or diesel range fuels, or etherified with an alcohol such as methanol or ethanol making ether as a gasoline blend (e.g., MTBE or ETBE from iso-butane).

Steps 1 and 2 have been previously described with respect to mixed paraffinic feedstocks in applicant' application, U.S. Publ. App. No. 2016/0168048, incorporated by reference herein in its entirety. U.S. Publ. App. No. 2016/0168048 describes a process to convert light paraffins to heavier hydrocarbons generally, for example, distillates and lubricant base stocks, using coupling chemistry analogous to Steps 1-3 described above. Whereas U.S. Publ. App. No. 2016/0168048 is directed to mixed paraffinic feed to create distillates and lubricant base stocks, certain embodiments utilize analogous coupling chemistry to create a tailored paraffinic hydrocarbon fluid utilizing iso-paraffinic feedstock. U.S. Publ. App. No. 2016/0168048 further discloses upgrading raw refinery feeds, such as natural gas liquids, liquid petroleum gas, and refinery light gas such as light virgin naphtha (LVN) or light catalytic naphtha (LCN), using coupling chemistry.

Iso-butane oxidation in Step 1 is well-established commercially for making t-butyl hydroperoxide (TBHP) for propylene oxide manufacture, with variants of the process also described, for example, in U.S. Pat. Nos. 2,845,461; 3,478,108; 4,408,081 and 5,149,885. EP 0567336 and U.S. Pat. No. 5,162,593 disclose co-production of TBHP and t-butyl alcohol (TBA). As TBA is another reactant used in Step 2 of the present disclosure, the present inventive process scheme utilizes Step 1 as a practical source of these two reactants. Air (~21% oxygen), a mixture of nitrogen and oxygen containing 2-20 vol % oxygen, or pure oxygen, can be used for the oxidation, as long as the oxygen-to-hydrocarbon vapor ratio is kept outside the explosive regime. Air can be used as the source of oxygen. Typical oxidation conditions for Step 1 of the present disclosure are: 110-150° C. (e.g, 130 to 140° C., at a pressure of about 300-800 psig (e.g., about 450-550 psig), with a residence time of 2-24 hours (preferably 6-8 h), to give a targeted conversion of 15%-70% (e.g., 30-50%). Selectivity to TBHP of 50-80% and to TBA of 20-50% is typical.

In Step 2, the conversion of the TBHP and TBA to di-t-butyl peroxide (DTBP) is performed using an acid catalyst. For example, U.S. Pat. No. 5,288,919 describes the use of an inorganic heteropoly and/or isopoly acid catalyst (such as for the reaction of TBA with TBHP. The conjoint production of DTBP and TBA from TBHP is also described in U.S. Pat. No. 5,345,009. One configuration for the present disclosure uses reactive distillation where product water is continuously removed as overhead by-product. Typical reaction temperature is in the range of 50-200° C.; 60-150° C.; or 80-120° C. The TBHP to TBA mole ratio is in the range of 0.5-2; 0.8-1.5; or 0.9-1.1. The reaction can be performed with or without a solvent. Suitable solvents comprise hydrocarbons having a carbon number greater than 3, such as paraffins, naphthenes, or aromatics. Conveniently, the unreacted iso-butane from Step 1 can be used as solvent for Step 2. Pressure for the reaction is held at appropriate ranges to ensure the reaction occurs substantially in the liquid phase, for example, 0-300 psig; 5-100 psig; or 15-50 psig. An acid catalyst such as Amberlyst™ resin, Nafion™ resin, aluminosilicates, acidic clay, zeolites (natural or synthetic), silicoaluminophosphates (SAPO), heteropolyacids, acidic oxides such as tungsten oxide on zirconia, molybdenum oxide on zirconia, sulfated zirconia, liquid acids such sulfuric acid, or acidic ionic liquids may be used in Step 2/Equation 2 to promote the conversion of TBHP and TBA into DTBP.

In Step 3/Equation 3, DTBP is introduced to a coupling reactor to initiate free radical coupling of iso-butane feed. Typical reaction conditions for Step 3 of the present disclosure are: 100-170° C. (e.g., about 145-155° C.), with pressure maintained to ensure that iso-butane stays in the liquid or supercritical phase, typically 700-1500 psig (e.g., about 850-950 psig). Residence time is normally in the range of 2-24 hours (e.g., 4-16 hours). The molar ratio of DTBP to iso-butane to be coupled is in the range of about 0.01-100, preferably in the range of about 0.05-10, and more preferably in the range of 0.1-2. Complete conversion of DTBP is normally achieved in this step.

Following Step 3, the mixed products may then fractionated to remove unreacted iso-butane and TBA, byproduct acetone, and to separate high octane gasoline as well as jet-range hydrocarbons.

Gasoline Compositions

In another aspect, the disclosure provides a gasoline composition having a road octane (RON) greater than 100. In certain embodiments, the road octane is greater than 103; greater than 111042; or greater than 110.

In another aspect, the disclosure provides a gasoline composition produced by the methods of the disclosure described herein.

Specifically, the disclosure provides a gasoline composition prepared by a process which involves three primary steps: (1) oxidizing one or more iso-paraffins to alkyl hydroperoxides and alcohol using air or oxygen; (2) converting the alkyl hydroperoxides and alcohol to dialkyl peroxide; and (3) radical-initiated coupling two or more light paraffins and/or light hydrocarbons using the dialkyl peroxide as a radical initiator to form a gasoline composition comprising gasoline range molecules. The products may then be optionally fractionated to isolate the gasoline fraction having a road octane number (RON) greater than 100.

In certain embodiments of the present disclosure, the disclosure provides a gasoline composition prepared by a process comprising the steps of: (1) oxidizing iso-butane to t-butyl hydroperoxide and t-butyl alcohol using air or oxygen; (2) converting the t-butyl hydroperoxide and t-butyl alcohol to di-t-butyl peroxide; and (3) radical-initiated coupling of two or more light parrafins and/or light hydrocarbons using the di-t-butyl peroxide as a radical initiator to form a gasoline composition comprising gasoline range molecules.

In certain embodiments, the light hydrocarbons coupled during the conversion step are a mixture are $C_3$-$C_8$ hydrocarbons. In certain embodiments, the hydrocarbons coupled during the conversion step are a mixture of $C_3$-$C_5$ hydrocarbons. In particular embodiments, the hydrocarbons coupled during the conversion step are a mixture of propane and isobutane; a mixture of isobutane and isopentane, a mixture of propane and isopentane, or a mixture of propane, isobutane, and isopentane.

In certain embodiments, the gasoline composition is produced without the use of a catalyst.

In another aspect, the disclosure provides a $C_7$ enriched gasoline composition. In certain embodiments, the $C_7$ enriched gasoline composition is produced by the methods of the disclosure described herein.

In particular embodiments, the gasoline composition is substantially free of sulfur. In another embodiment, the gasoline composition is substantially free of fluoride. In still another embodiment, the gasoline composition is substantially free of sulfur and fluoride.

The gasoline components and the methods of the disclosure can be used with and to the long term benefit of reciprocating engines of commercial and consumer vehicles, e.g., cars, trucks, motorcycles, and the like, and any other suitable applications.

EXAMPLES

In order to provide a better understanding of the foregoing disclosure, the following non-limiting examples are offered. Although the examples may be directed to specific embodiments, they are not to be viewed as limiting the disclosure in any specific respect.

Example 1: Propane and Isobutane (26940-152)

This example illustrates the general procedure for coupling propane and iso-butane using DTBP to form high octane gasoline. In a 300 cc autoclave 40 g of DTBP (trade name Luperox DI from Aldrich Chemicals, 98%) is loaded. The autoclave is sealed, connected to a gas manifold, and pressure tested under 600 psig nitrogen. The nitrogen is vented and 50 cc of liquid propane, 50 cc of liquid iso-butane (Airgas, instrument grade) are charged. The reactor content is heated under stirring (500 rpm) at a rate of 2° C./min to 150° C. and held for 4 hours. The heat is turned off and the autoclave allowed to cool down to room temperature. A sample is taken and analyzed by GC, showing complete conversion of DTBP. The autoclave is opened and the reactor content collected at the end of the run, recovering the materials loaded (88.6% of the materials are recovered after the reaction). The products are analyzed by GC. The run is repeated using different loadings of DTBP.

The procedure above was performed and the results are shown in Table 1 below.

TABLE 1

Product distribution from propane/isobutane coupling (Example 1)

| Product | Wt % |
|---|---|
| Neopentane | 0.2 |
| Acetone | 23.9 |
| 2-methyl butane | 0.3 |
| t-Butanol | 55.8 |
| isobutylene epoxide | 1.0 |
| *2,3-dimethyl butane* | *0.5* |
| 2-methyl pentane | 0.4 |
| 2,2-dimethly pentane | 1.0 |
| 2,4-dimethyl pentane | 0.6 |
| *2,2,3-trimethyl butane* | *2.5* |
| *2,2,4-trimethyl pentane* | *1.4* |
| *2,2,3,3-tetramethyl butane* | *2.4* |
| 5-methyl-2-hexanone | 1.2 |
| Other C4 | 0.1 |
| Other C6 | 0.1 |
| Other C7 | 0.3 |
| Other C8 | 1.1 |
| Other C9 | 0.4 |
| C10+ | 6.8 |

High octane products such as 2,3-dimethylbutane, 2,2,3-trimethylbutane (triptane), 2,2,4-trimethylpentane (iso-octane), and 2,2,3,3-tetramethylbutane (all shown in italics in Table 1) are formed from the reaction.

One of skill in the art will appreciate that key variables, including reaction temperature, molar ratio of DTBP to hydrocarbon, and residence time, can be adjusted to optimize and tailor the gasoline fraction for specific applications.

Example 2: Isopentane and Isobutane (26940-154)

This example illustrates the general procedure for coupling iso-pentane and isobutane using DTBP to form high octane gasoline. In a 300 cc autoclave 56 g of DTBP (trade name Luperox DI from Aldrich Chemicals, 98%) and 50 cc (29 g) of iso-pentane are loaded. The autoclave is sealed, connected to a gas manifold, and pressure tested under 600 psig nitrogen. The nitrogen is vented and 50 cc of liquid isobutane (Airgas, instrument grade) is charged. The reactor content is heated under stirring (500 rpm) at a rate of 2° C./min to 150° C. and held for 4 hours. The heat is turned off and the autoclave allowed to cool down to room temperature. A sample is taken and analyzed by GC, showing complete conversion of DTBP. The autoclave is opened and the reactor content collected at the end of the run, recovering the materials loaded [(100±5)% of the materials are recovered after the reaction]. The products are analyzed by GC. The run is repeated using different loadings of DTBP. The procedure above was performed and the results are shown in Table 2 below.

TABLE 2

Product distribution from iso-pentane/iso-butane coupling (Example 2)

| Product | Wt % |
|---|---|
| Neopentane | 0.2 |
| Acetone | 21.4 |
| t-Butanol | 58.6 |
| isobutylene epoxide | 1.0 |
| 2,3-dimethyl butane | 0.1 |
| 3-methyl pentane | 0.2 |
| *2,2,4-trimethyl pentane* | *1.7* |
| *2,2,3,3-tetramethyl butane* | *2.1* |
| 2,2,5-trimethyl hexane | 0.3 |
| 2,2,4-trimethyl hexane | 0.7 |
| 2,4,4-trimethyl hexane | 0.6 |
| 2,3,5-trimethyl hexane | 0.2 |
| *2,2,3,4-tetramethyl pentane* | *0.8* |
| 2,2,3-trimethyl hexane | 0.1 |
| 4-ethyl-2-methyl hexane | 0.1 |
| 5-methyl-2-hexanone | 1.2 |
| *2,2,3,3-tetramethyl pentane* | *1.8* |
| 3,3,4-trimethyl heptane | 0.4 |
| 3-ethyl-4-methylheptane | 0.5 |
| 4-methyl nonane | 0.1 |
| 2,2,4,4,5,5,7,7-octamethyloctane | 0.7 |
| Other C4 | 0.1 |
| Other C5 | 0.3 |
| Other C6 | 0.2 |
| Other C8 | 0.4 |
| Other C9 | 0.1 |
| Other C10 | 1.2 |
| C10+ | 4.8 |

High octane products such as 2,2,4-trimethylpentane (iso-octane), 2,2,3,3-tetramethylbutane, 2,2,3,4-tetramethyl pentane, and 2,2,3,3-tetramethyl pentane (all shown in italics in Table 2) are formed from the reaction.

Example 3: n-pentane and Isobutane (26940-153)

This example illustrates the general procedure for coupling n-pentane and iso-butane using DTBP to form high octane gasoline. In a 300 cc autoclave the following are loaded: 50 cc of n-pentane, and 60 g of DTBP (trade name Luperox DI from Aldrich Chemicals, 98%). The autoclave is sealed, connected to a gas manifold, and pressure tested under 600 psig nitrogen. The nitrogen is vented and 50 cc of liquid iso-butane (Airgas, instrument grade) is charged. The reactor content is heated under stirring (500 rpm) at a rate of 2° C./min to 150° C. and held for 4 hours. The heat is turned off and the autoclave allowed to cool down to room temperature. A sample is taken and analyzed by GC, showing complete conversion of DTBP. The autoclave is opened and the reactor content collected at the end of the run, recovering the materials loaded [(100±3)% of the materials are recovered after the reaction]. The products are analyzed by GC. The run is repeated using different loadings of DTBP. The procedure above was performed and the results are shown in Table 3 below.

TABLE 3

Product distribution from n-pentane/
iso-butane coupling (Example 3)

| Product | Wt % |
| --- | --- |
| Neopentane | 0.3 |
| Acetone | 21.9 |
| 2-methyl butane | 0.4 |
| t-Butanol | 59.0 |
| isobutylene epoxide | 1.1 |
| 2-methyl pentane | 0.2 |
| 3-methyl pentane | 0.1 |
| n-hexane | 0.1 |
| *2,2,4-trimethyl pentane* | *1.5* |
| *2,2,3,3-tetramethyl butane* | *2.3* |
| 2,2-dimethly heptane | 0.7 |
| *2,2,3,4-tetramethyl pentane* | *0.9* |
| *2,2,3-trimethly hexane* | *3.0* |
| 4-ethyl-2-methyl hexane | 0.2 |
| 5-methyl-2-hexanone | 1.2 |
| 4-methyl-2-heptanone | 0.1 |
| 3-ethyl-4-methylheptane | 0.5 |
| 4,5-dimethly octane | 0.3 |
| 4-methyl nonane | 0.2 |
| 2,2,4,4,5,5,7,7-octamethyloctane | 0.6 |
| Other C4 | 0.1 |
| Other C5 | 0.1 |
| Other C8 | 0.3 |
| Other C9 | 0.6 |
| Other C10 | 1.0 |
| C10+ | 3.3 |

High octane products such as 2,2,4-trimethylpentane (iso-octane), 2,2,3,3-tetramethylbutane, 2,2,3,4-tetramethyl pentane, and 2,2,3-trimethly hexane (all shown in italics in Table 2) are formed from the reaction.

Example 4: Propane and Isopentane

This example illustrates the general procedure for coupling propane and iso-pentane using DTBP to form high octane gasoline. In a 300 cc autoclave the following are loaded: 50 cc of propane, 50 cc of iso-pentane (Airgas, instrument grade) and 56 g of DTBP (trade name Luperox DI from Aldrich Chemicals, 98%). The autoclave is sealed, connected to a gas manifold, and pressurized with 600 psig nitrogen. The reactor content is heated under stirring (500 rpm) at a rate of 2° C./min to 150° C. and held for 4 hours. The heat is turned off and the autoclave allowed to cool down to room temperature. A sample is taken and analyzed by GC, showing complete conversion of DTBP. The autoclave is opened and the reactor content collected at the end of the run, recovering the materials loaded. The products are analyzed by GC. The run is repeated using different loadings of DTBP.

Example 5: Propane, Isobutane and Isopentane

This example illustrates the general procedure for coupling propane, iso-butane, and iso-pentane using DTBP to form high octane gasoline. In a 300 cc autoclave the following are loaded: 33 cc of propane, 34 cc of iso-butane, and 33 cc of iso-pentane (Airgas, instrument grade) and 56 g of DTBP (trade name Luperox DI from Aldrich Chemicals, 98%). The autoclave is sealed, connected to a gas manifold, and pressurized with 600 psig nitrogen. The reactor content is heated under stirring (500 rpm) at a rate of 2° C./min to 150° C. and held for 4 hours. The heat is turned off and the autoclave allowed to cool down to room temperature. A sample is taken and analyzed by GC, showing complete conversion of DTBP. The autoclave is opened and the reactor content collected at the end of the run, recovering the materials loaded. The products are analyzed by GC. The run is repeated using different loadings of DTBP.

Example 6: Bio-Fuel Propane and Isobutane

This example illustrates the general procedure for coupling propane and iso-butane from bio sources using DTBP to form high octane gasoline.

In a 300 cc autoclave the following are loaded: 50 cc of bio-propane, 50 cc of bio-iso-butane (Airgas, instrument grade) and 56 g of DTBP (trade name Luperox DI from Aldrich Chemicals, 98%). The autoclave is sealed, connected to a gas manifold, and pressurized with 600 psig nitrogen. The reactor content is heated under stirring (500 rpm) at a rate of 2° C./min to 150° C. and held for 4 hours. The heat is turned off and the autoclave allowed to cool down to room temperature. A sample is taken and analyzed by GC, showing complete conversion of DTBP. The autoclave is opened and the reactor content collected at the end of the run, recovering the materials loaded. The products are analyzed by GC. The run is repeated using different loadings of DTBP.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired products, additional ingredients may be added, and/or similar ingredients may be substituted for one or more of the ingredients described.

Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

PCT/EP Clauses:

Clause 1. A process for the production of a high octane gasoline composition comprising gasoline-range molecules, the process comprising the steps of:
(a) providing a first feed stream comprising one or more iso-paraffins and oxiding the iso-parrafins to form alkyl hydroperoxides and alcohol;
(b) converting the alkyl hydroperoxides and alcohols to dialkyl peroxides; and
(c) providing a second feed stream comprising two or more light paraffins or light hydricarbons and coupling the light paraffins and/or light hydrocarbons using the dialkyl peroxides as a radical initiator to form a gasoline composition comprising gasoline-range molecules;
(d) optionally fractionating the gasoline-range molecules to isolate a desired gasoline fraction having a road octane number (RON) greater than about 100.

Clause 2. The process of clause 1, wherein the one or more iso-paraffins in the first feed stream is iso-butane.

Clause 3. The process of any one of clauses 1-2, wherein the second feed stream comprises two or more C3-C8 paraffins or two or more C3-C8 hydrocarbons.

Clause 4. The process of any one of clauses 1-3, wherein the second feed stream comprises two or more C3-C5 paraffins or two or more C3-C5 hydrocarbons.

Clause 5 The process of any one of clauses 1-4, wherein the second feed stream comprises a mixture of propane and isobutane; a mixture of isobutane and isopentane, a mixture of propane and isopentane, or a mixture of propane, isobutane, and isopentane.

Clause 6. The process of any one of clauses 1-5, wherein the second feed stream comprises a mixture of propane and isobutane.

Clause 7. The process of any one of clauses 1-6, wherein the process is performed without a catalyst.

Clause 8. The process of any one of clauses 1-7, wherein the iso-paraffins, the light paraffins, and/or the light hydrocarbons are biologically derived.

Clause 9. A process for the production of a high octane gasoline composition comprising gasoline-range molecules, the process comprising the steps of:
(a) providing a first feed stream comprising isobutane and oxidizing the isobutane to form a t-butyl hydroperoxide and t-butyl alcohol;
(b) converting the t-butyl hydroperoxide and t-butyl alcohol to t-butyl alcohol to di-t-butyl peroxide; and
(c) providing a second feed stream comprising two or more light paraffins or light hydricarbons and coupling the light paraffins and/or light hydrocarbons using the di-t-butyl peroxide as a radical initiator to form a gasoline composition comprising gasoline-range molecules;
(d) optionally fractionating the gasoline-range molecules to isolate a desired gasoline fraction having a road octane number (RON) greater than about 100.

Clause 10. The process of clause 9, wherein the process is performed without a catalyst.

Clause 11. The process of any one of clauses 9-10, wherein the iso-paraffins, the light paraffins, and/or the light hydrocarbons are biologically derived.

Clause 12. A high octane gasoline composition prepared according to any one of clauses 1-8.

Clause 13. A high octane gasoline composition prepared according to any one of clauses 9-11.

Clause 14. The high octane gasoline composition of any one of clauses 12-13, which is substantially free of sulfur, fluoride, or both.

Clause 15. The high octane gasoline composition of any one of clauses 12-14, wherein the high octane gasoline composition is a C7 enriched gasoline composition.

What is claimed is:

1. A process for the production of a high octane gasoline composition comprising gasoline-range molecules, wherein the high octane gasoline composition is a C7 enriched gasoline composition, the process comprising the steps of:
(a) providing a first feed stream comprising one or more iso-paraffins and oxidizing the iso-paraffins to form alkyl hydroperoxides and alcohol;
(b) converting the alkyl hydroperoxides and alcohols to dialkyl peroxides; and
(c) providing a second feed stream comprising two or more light paraffins or light hydrocarbons and coupling the light paraffins and/or light hydrocarbons using the dialkyl peroxides as a radical initiator to form a gasoline composition comprising gasoline-range molecules;
(d) optionally fractionating the gasoline-range molecules to isolate a gasoline fraction having a road octane number (RON) greater than about 100.

2. The process of claim 1, wherein the one or more iso-paraffins in the first feed stream is iso-butane.

3. The process of claim 1, wherein the second feed stream comprises two or more C3-C8 paraffins.

4. The process of claim 1, wherein the second feed stream comprises two or more C3-C8 hydrocarbons.

5. The process of claim 3, wherein the second feed stream comprises two or more C3-C5 paraffins.

6. The process of claim 4, wherein the second feed stream comprises two or more C3-C5 hydrocarbons.

7. The process of claim 6, wherein the second feed stream comprises a mixture of propane and isobutane; a mixture of isobutane and isopentane, a mixture of propane and isopentane, or a mixture of propane, isobutane, and isopentane.

8. The process of claim 7, wherein the second feed stream comprises a mixture of propane and isobutane.

9. The process of claim 1, wherein the process is performed without a catalyst.

10. The process of claim 1, wherein the iso-paraffins, the light paraffins, and/or the light hydrocarbons are biologically derived.

11. A process for the production of a high octane gasoline composition comprising gasoline-range molecules, wherein the high octane gasoline composition is a C7 enriched gasoline composition, the process comprising the steps of:
(a) providing a first feed stream comprising isobutane and oxidizing the isobutane to form a t-butyl hydroperoxide and t-butyl alcohol;
(b) converting the t-butyl hydroperoxide and t-butyl alcohol to t-butyl alcohol to di-t-butyl peroxide; and
(c) providing a second feed stream comprising two or more light paraffins or light hydrocarbons and coupling the light paraffins and/or light hydrocarbons using the di-t-butyl peroxide as a radical initiator to form a gasoline composition comprising gasoline-range molecules;
(d) optionally fractionating the gasoline-range molecules to isolate a gasoline fraction having a road octane number (RON) greater than about 100.

12. The process of claim 11, wherein the process is performed without a catalyst.

13. The process of claim 11, wherein the iso-paraffins, the light paraffins, and/or the light hydrocarbons are biologically derived.

14. A high octane gasoline composition prepared according to claim wherein the high octane gasoline composition is a C7 enriched gasoline composition.

15. A high octane gasoline composition prepared according to claim 11, wherein the high octane gasoline composition is a C7 enriched gasoline composition.

16. The high octane gasoline composition of claim 15 which is substantially free of sulfur, fluoride, or both.

* * * * *